US012048511B2

(12) United States Patent
Asghar et al.

(10) Patent No.: US 12,048,511 B2
(45) Date of Patent: Jul. 30, 2024

(54) SYSTEMS AND METHODS FOR DETECTING DISEASE USING MOBILE DEVICE

(71) Applicant: FLORIDA ATLANTIC UNIVERSITY BOARD OF TRUSTEES, Boca Raton, FL (US)

(72) Inventors: Waseem Asghar, Boca Raton, FL (US); Benjamin Coleman, Houston, TX (US); Chad Coarsey, Boca Raton, FL (US)

(73) Assignee: FLORIDA ATLANTIC UNIVERSITY BOARD OF TRUSTEES, Boca Raton, FL (US)

( * ) Notice: Subject to any disclaimer, the term of this patent is extended or adjusted under 35 U.S.C. 154(b) by 509 days.

(21) Appl. No.: 17/311,893

(22) PCT Filed: Oct. 21, 2019

(86) PCT No.: PCT/US2019/057216
§ 371 (c)(1),
(2) Date: Jun. 8, 2021

(87) PCT Pub. No.: WO2020/131210
PCT Pub. Date: Jun. 25, 2020

(65) Prior Publication Data
US 2022/0026275 A1    Jan. 27, 2022

Related U.S. Application Data

(60) Provisional application No. 62/782,807, filed on Dec. 20, 2018.

(51) Int. Cl.
*A61B 5/00* (2006.01)
*G01J 3/28* (2006.01)
(Continued)

(52) U.S. Cl.
CPC .......... *A61B 5/0077* (2013.01); *G01J 3/2823* (2013.01); *G06V 10/17* (2022.01); *G06V 10/25* (2022.01); *G06V 10/56* (2022.01); *G06V 20/48* (2022.01)

(58) Field of Classification Search
None
See application file for complete search history.

(56) References Cited

U.S. PATENT DOCUMENTS 11,181,482 B1\* 11/2021 Pyayt ..................... G01N 21/29
2015/0055134 A1\* 2/2015 Papautsky ............ G01N 21/278
356/402

(Continued)

OTHER PUBLICATIONS

International Search Report for corresponding PCT Application No. PCT/US2018/057216 dated Jan. 14, 2020.
(Continued)

*Primary Examiner* — Leon Flores
(74) *Attorney, Agent, or Firm* — Meunier Carlin & Curfman LLC (57) ABSTRACT

A video processing method improves the repeatability of point-of-care (POC) mean pixel intensity (MPI) analysis, for example by rejecting low-quality input data using image features. Using these features, the method selects high-quality frames and achieves an improvement in correlation and standard error for the MPI-absorbance relationship. In another example, a mobile device (e.g., smartphone) based image processing method produces an MPI output with smaller variances, lower limits of detection (LODs), and a higher dynamic range than existing methods. This method has improved performance in the presence of additive and multiplicative ambient light noise.

19 Claims, 5 Drawing Sheets

(51) Int. Cl.
G06V 10/10 (2022.01)
G06V 10/25 (2022.01)
G06V 10/56 (2022.01)
G06V 20/40 (2022.01)

(56) References Cited

U.S. PATENT DOCUMENTS

2018/0293350 A1* 10/2018 Dimov .................. G16H 50/20
2018/0299473 A1* 10/2018 Chou ..................... G16Z 99/00

OTHER PUBLICATIONS

Abstract of Coleman et al., "Point-of-Care Colorimetric Analysis Through Smartphone Video", Sensors and Actuators B:Chemical, vol. 282, pp. 225-231 (2019).
Vashist et al., "Emerging Technologies for Next-Generation Point-of-Care Testing", Trends in Biotechnology, vol. 33, No. 11, pp. 692-705 (2015).
Wang et al., "Integration of Cell Phone Imaging With Microchip ELISA to Detect Ovarian Cancer HE4 Biomarker in Urine at the Point-of-Care", Lab on a Chip, vol. 11, pp. 3411-3418 (2011).
Zhu et al., "Cost-Effective and Rapid Blood Analysis on a Cell-Phone", Lab on a Chip, vol. 13, pp. 1282-1288 (2013).
Pollock et al., "A Paper-Based Multiplexed Transaminase Test for Low-Cost Point-of-Care Liver Function Testing", Science Translational Medicine, vol. 4, pp. 152ra129 (2012).
Shafiee et al., "Emerging Technologies for Point-of-Care Management of HIV Infection", Annual Review of Medicine, vol. 66, pp. 387-405 (2015).
Veigas et al., "Gold on Paper-Paper Platform for Au-nanoprobe TB Detection", Lab on a Chip, vol. 12, pp. 4802-4808, (2012).
Zhu et al., "Cost-Effective and Compact Wide-Field Fluorescent Imaging on a Cell Phone", Lab on a Chip, vol. 11, pp. 315-322 (2011).
Chen et al., "Detection of Mercury(II) Ions Using Colorimetric Gold Nanoparticles on Paper-Based Analytical Devices", Analytical Chemisry, American Cancer Society, vol. 86, pp. 6843-6849 (2014).
Wei et al., "Detection and Spatial Mapping of Mercury Contamination in Water Samples Using a Smart-Phone", ACS Nano, vol. 8, No. 2, pp. 1121-1129 (2014).
Sumriddetchkajorn et al., "Mobile Device-Based Self-Referencing Colorimeter for Monitoring Chlorine Concentration in Water", Sensors and Actuators B: Chemical, vol. 182, pp. 592-597 (2013).
Salles et al., "Explosive Colorimetric Discrimination Using a Smartphone, Paper Device and Chemometrical Approach," Analytical Methods, vol. 6, No. 7, pp. 2047-2052 (2014).
McGeough et al., "Camera Phone-Based Quantitative Analysis of C-Reactive Protein ELISA", IEEE Transactions on Biomedical Circuits and Systems, vol. 7, No. 5, pp. 655-659 (2013).
McGonigle et al., "Smartphone Spectrometers", Sensors, vol. 18, p. 223 (2018).
Murdock et al., "Optimization of a Paper-Based ELISA for a Human Performance Biomarker", Analytical Chemisty, vol. 85, pp. 11634-11642 (2013).
Ogirala et al., "Smartphone-Based Colorimetric ELISA Implementation for Determination of Women's Reproductive Steroid Hormone Profiles", Medical & Biological Engineering & Computing, vol. 55, pp. 1735-1741 (2017).
Berg et al., "Cellphone-Based Hand-Held Microplate Reader for Point-of-Care Testing of Enzyme-Linked Immunosorbent Assays," ACS Nano, vol. 9, No. 8, pp. 7857-7866 (2015). 2015.
Bland et al., "Comparing Methods of Measurement: Why Plotting Difference Against Standard Method is Misleading", The Lancet, vol. 346, pp. 1085-1087 (1995).
Kim et al., "A Smartphone-Based Optical Platform for Colorimetric Analysis of Microfluidic Device", Sensors and Actuators B: Chemical, vol. 239, pp. 52-59 (2017).
Shen et al., "Point-of-Care Colorimetric Detection With a Smartphone", Lab on a Chip, vol. 12, pp. 4240-4243 (2012).
McCracken et al., "Recent Approaches for Optical Smartphone Sensing in Resource-Limited Settings: A Brief Review", Analytical Methods, vol. 8, pp. 6591-6601 (2016).
Roda et al., "Smartphone-Based Biosensors: A Critical Review and Perspectives," Trends in Analytical Chemistry, vol. 79, pp. 317-325 (2016).
Mudanyali et al., "Integrated Rapid-Diagnostic-Test Reader Platform on a Cellphone", Lab on a Chip, vol. 12, pp. 2678-2686 (2012).
Vashist et al., "A Smartphone-Based Colorimetric Reader for Bioanalytical Applications Using the Screen-Based Bottom Illumination Provided by Gadgets", Biosensors and Bioelectronics, vol. 67, pp. 248-255 (2015).
Sumriddetchkajorn et al., "Mobile-Platform Based Colorimeter for Monitoring Chlorine Concentration in Water", Sensors and Actuators B: Chemical, vol. 191, pp. 561-566 (2014).
Yetisen et al., "A Smartphone Algorithm With Inter-Phone Repeatability for the Analysis of Colorimetric Tests", Sensors and Actuators B: Chemical, vol. 196, pp. 156-160 (2014).
Oncescu et al., "Smartphone Based Health Accessory for Colorimetric Detection of Biomarkers in Sweat and Saliva", Lab on a Chip, vol. 13, pp. 3232-3238 (2013).
Hong et al., "Development of the Smartphone-Based Colorimetry for Multi-Analyte Sensing Arrays," Lab on a Chip, vol. 14, pp. 1725-1732 (2014).
Krauss et al., "Color Manipulation Through Microchip Tinting for Colorimetric Detection Using Hue Image Analysis", Lab on a Chip, vol. 17, pp. 4089-4096 (2017).
Oncescu et al., "Cholesterol Testing on a Smartphone", Lab on a Chip, vol. 14, pp. 759-763 (2014).
Battisti et al., "Hue-Based Quantification of Mechanochromism Towards a Cost-Effective Detection of Mechanical Strain in Polymer Systems", Chemical Communications, vol. 53, pp. 248-251 (2017).
McCracken et al., "Multimodal Imaging and Lighting Bias Correction for Improved μPAD-Based Water Quality Monitoring via Smartphones", Scientific Reports, vol. 6, pp. 1-13 (2016).
Dell et al., "Towards a Point-of-Care Diagnostic System: Automated Analysis of Immunoassay Test Data on a Cell Phone", Proceedings of the 5th ACM Workshop on Networked Systems For Developing Regions (2011).
Pech-Pacheco et al., "Diatom Autofocusing in Brightfield Microscopy: A Comparative Study", Proceedings of the 15th International Conference on Pattern Recognition (2000).
Hanneman, K., "Design, Analysis and Interpretation of Method-Comparison Studies", AACN Advanced Critical Care, vol. 19, No. 2, pp. 223-224 (2008).
Zhu et al., Optical Imaging Techniques for Point-of-Care Diagnostics, Lab on a Chip, vol. 13, pp. 51-67 (2013).
Zhu et al., "Quantum Dot Enabled Detection of *Escherichia coli* Using a Cellphone", Analyst, vol. 137, pp. 2541-2544 (2012).
Kadlec et al., "A Cell Phone-Based Microphotometric System for Rapid Antimicrobial Susceptibility Testing", Journal of Laboratory Automation, vol. 19, pp. 258-266 (2014).
O'Driscoll et al., "A Novel Camera Phone-Based Platform for Quantitative Fluorescence Sensing", Analytical Methods, vol. 5, No. 8, pp. 1889-2136 (2013).
Lin et al., "A Lateral Electrophoretic Flow Diagnostic Assay", Lab on a Chip, vol. 15, pp. 1488-1496 (2015).
Lee et al., A Low-Cost, High-Performance System for Fluorescence Lateral Flow Assays, Biosensors, vol. 3, pp. 360-373 (2013).
Yetisen et al., "Paper-Based Microfluidic Point-of-Care Diagnostic Devices", Lab on a Chip, vol. 13, pp. 2210-2251 (2013).
Shafiee et al., "Paper and Flexible Substrates as Materials for Biosensing Platforms to Detect Multiple Biotargets", Scientific Reports, vol. 5, No. 8719, pp. 1-9 (2015).
Contreras-Naranjo et al., "Mobile Phone-Based Microscopy, Sensing, and Diagnostics", IEEE Journal of Selected Topics in Quantum Electronics, vol. 22, No. 3, pp. 392-405 (2016).
Martinez et al., "Simple Telemedicine for Developing Regions: Camera Phones and Paper-Based Microfluidic Devices for Real-Time, Off-Site Diagnosis", Analytical Chemistry, vol. 80, No. 10, pp. 3699-3707 (2008).

(56) References Cited

OTHER PUBLICATIONS

Abstract of Sandoz et al., "Digital Readout Platform for Water-in-Oil Droplet Immunoassays Running on a Cell-Phone for Point of Care Viral Load Sensing", Proceedings of the 16th International Conference on Miniaturized Systems for Chemistry and Life Sciences, MicroTAS, (2012).

Kaoutit et al., "Sub-ppm Quantification of Hg(II) In Aqueous Media Using Both The Naked And Digital Information from Pictures of a Colorimetric Sensory Polymer Membrane Taken With The Digital Camera of a Conventional Mobile Phone", Analytical Methods, vol. 5, pp. 54-58 (2013).

Hosu et al., "Smartphone-Based Immunosensor for CA125 Detection", Talanta, vol. 166, pp. 234-240 (2017).

Urdea et al., "Requirements for High Impact Diagnostics in the Developing World", Nature, vol. 444, pp. 73-79 (2006).

Skandarajah et al., "Quantitative Imaging with a Mobile Phone Microscope", PLOS One, vol. 9, Issue 5 (2014).

Bao et al., "A Remote Computing Based Point-of-Care Colorimetric Detection System With a Smartphone Under Complex Ambient Light Conditions", Analyst, vol. 143, pp. 1387-1395 (2018).

Zhu et al., "Optofluidic Fluorescent Imaging Cytometry on a Cell Phone", Analytical Methods, No. 83, pp. 6641-6647 (2011).

Pandori et al., "Assessment of the Ability of a Fourth-Generation Immunoassay for Human Immunodeficiency Virus (HIV) Antibody and p24 Antigen To Detect both Acute and Recent HIV Infections in a High-Risk Setting", Journal of Clinical Microbiology, vol. 47, No. 8, pp. 2639-2642 (2009).

Qiu et al., "Comparative Evaluation of Three FDA-Approved HIV Ag/Ab Combination Tests Using a Genetically Diverse HIV Panel and Diagnostic Specimens", Journal of Clinical Virology, vol. 92, pp. 62-68 (2017).

Beelaert et al., "Evaluation of a Rapid and Simple Fourth-Generation HIV Screening Assay for Qualitative Detection of HIV p24 Antigen and/or Antibodies to HIV-1 and HIV-2", Journal of Virological Methods, vol. 168, pp. 218-222 (2010).

Binsbergen et al., "Strongly Enhanced Sensitivity of a Direct Anti-HIV-1:-2 Assay in Seroconversion by Incorporation of HIV p24 ag Detection: A New Generation Vironostika HIV Uni-Form II", Journal of Virological Methods, vol. 76, pp. 59-71 (1998).

Bystryak et al., "Detection of HIV-1 p24 Antigen in Patients With Varying Degrees of Viremia Using an ELISA With a Photochemical Signal Amplification System", Clinica Chimica Acta, vol. 456, pp. 128-136 (2016).

Schacker et al., "Clinical and Epidemiologic Features of Primary HIV Infection", Annals of Internal Medicine, vol. 124, No. 4 pp. 257-264 (1996).

Brust et al., "Shortening of the Diagnostic Window With a New Combined HIV p24 Antigen and Anti-HIV-1:2:O Screening Test", Journal of Virological Methods, vol. 90, pp. 153-165 (2000).

* cited by examiner

SYSTEMS AND METHODS FOR DETECTING DISEASE USING MOBILE DEVICE

CROSS-REFERENCE TO RELATED APPLICATIONS

This application is a U.S. National Phase Application under 35 U.S.C. § 371 of PCT/US2019/057216, filed Oct. 21, 2019, which claims priority to U.S. Provisional Application No. 62/782,807, filed Dec. 20, 2018, the contents of which are incorporated herein by reference in their entireties.

STATEMENT REGARDING FEDERALLY SPONSORED RESEARCH OR DEVELOPMENT

This invention(s) was made with government support under grant number R15AI127214 awarded by the National Institutes of Health. The government has certain rights in the invention(s).

FIELD OF DISCLOSURE

The disclosure relates to handheld mobile device image processing. In particular, the disclosure relates to image processing and analysis of analytes via a hand held mobile device.

BACKGROUND

Point-of-care (POC) tests often rely on smartphone image methods for colorimetric analysis, but the results of such methods are frequently difficult to reproduce or standardize. The problem is aggravated by unpredictable image capture conditions, which pose a significant challenge when low limits of detection (LOD) are needed. Application-specific smartphone attachments are often used to standardize imaging conditions, but there has recently been an interest in equipment-free point-of-care colorimetric analysis. Improved output metrics and preprocessing methods have been developed, but equipment-free imaging often has a high LOD and is inappropriate for quantitative tasks.

SUMMARY

The following presents a simplified summary in order to provide a basic understanding of some aspects of one or more embodiments or examples of the present invention. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later. Additional goals and advantages will become more evident in the description of the figures, the detailed description of the disclosure, and the claims.

The approach advocated in this application is a portable cost effective approach for improving remote portable point-of-care disease detection. The approach, which is explained in greater detail by examples discussed below, improves the functioning of smartphones or other portable computers, at least by decreasing necessary low limits of detection in half. The approach is important for a better management of the detected disease and reducing medical cost.

The approach advocated in this application includes a video processing method that may synthesize many images into a single output metric. An exemplary method may use image features to select the best inputs from a large set of video frames. The resulting output values may have a stronger correlation with laboratory methods and a lower standard error. The approach may only require 20 seconds of video and can easily be integrated with related processing methods. In an example, the method is applied to the NS1-based sandwich ELISA for Zika detection, and shows that the limits of detection is much lower, such as two times lower when the video-based method is used.

Further, an exemplary method uses the saturation parameter of hue-saturation-value colorpace to enable point-of-care diagnosis in the field. Through the analysis of over 10,000 images, the saturation method consistently outperforms current approaches under a wide range of operating field conditions. Performance improvement may be proven analytically via the mathematic relationship between the saturation method and existing techniques. In examples, methods do not require any light box or external equipment before imaging.

Exemplary embodiments are described herein. It is envisioned, however, that any system that incorporates features of apparatus and systems described herein are encompassed by the scope and spirit of the exemplary embodiments.

BRIEF DESCRIPTION OF THE DRAWINGS

Various exemplary embodiments of the disclosed apparatuses, mechanisms and methods will be described, in detail, with reference to the following drawings, in which like referenced numerals designate similar or identical elements, and.

DETAILED DESCRIPTION

Illustrative examples of the devices, systems, and methods disclosed herein are provided below. An embodiment of the devices, systems, and methods may include any one or more, and any combination of, the examples described below. This invention may, however, be embodied in many different forms and should not be construed as limited to the embodiments set forth below. Rather, these exemplary embodiments are provided so that this disclosure will be thorough and complete, and will fully convey the scope of the invention to those skilled in the art. Accordingly, the exemplary embodiments are intended to cover all alternatives, modifications, and equivalents as may be included within the spirit and scope of the apparatuses, mechanisms and methods as described herein.

The inventors initially point out that description of well-known starting materials, processing techniques, components, equipment and other well-known details may merely be summarized or are omitted so as not to unnecessarily obscure the details of the present disclosure. Thus, where details are otherwise well known, we leave it to the application of the present disclosure to suggest or dictate choices relating to those details. The drawings depict various examples related to embodiments of illustrative methods, apparatus, and systems for inking from an inking member to the reimageable surface.

The modifier "about" used in connection with a quantity is inclusive of the stated value and has the meaning dictated by the context (for example, it includes at least the degree of error associated with the measurement of the particular quantity). When used with a specific value, it should also be considered as disclosing that value.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. For example, "a plurality of resistors" may include two or more resistors.

When referring to any numerical range of values herein, such ranges are understood to include each and every number and/or fraction between the stated range minimum and maximum. For example, a range of 0.5-6% would expressly include all intermediate values of 0.6%, 0.7%, and 0.9%, all the way up to and including 5.95%, 5.97%, and 5.99%. The same applies to each other numerical property and/or elemental range set forth herein, unless the context clearly dictates otherwise.

The term enzyme-linked immunosorbent assay (ELISA) refers to a commonly used analytical biochemistry assay. The assay uses a solid-phase enzyme immunoassay (EIA) to detect the presence of a ligand (commonly a protein) in a liquid sample using antibodies directed against the protein to be measured. ELISA has been used as a diagnostic tool in medicine, plant pathology, and biotechnology, as well as a quality control check in various industries.

The term "microcontroller" is used herein generally to describe various apparatus relating to the operation of one or more devices that directs or regulates a process or machine. A microcontroller is a type of controller and can be implemented in numerous ways (e.g., such as with dedicated hardware) to perform various functions discussed herein. A "microprocessor" is one example of a microcontroller which employs one or more microprocessors that may be programmed using software (e.g., microcode) to perform various functions discussed herein. A microcontroller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs). By example, a microcontroller may include one or more microprocessors, memory and input/output (I/O) peripherals, possibly on a single chip.

A critical component of any point-of-care (POC) diagnostic system is the evaluation stage. Conventional laboratory equipment is usually too infrastructure-dependent, bulky, or expensive to be well-suited to resource-constrained settings. This poses challenges for tests that require precise measurements, making the measurement system a limiting factor for point-of-care detection and quantification.

Smartphones have been identified as a solution to the measurement problem because they are easily accessible, computationally powerful, and contain sophisticated sensors that can transmit data in real time from nearly anywhere in the world. The smartphone camera has found applications in microfluidics, microscopy, and the evaluation of paper-based devices. Since many assays produce a colorimetric response, cell phone imaging has emerged as a common method of smartphone-enabled point-of-care evaluation. Quantitative colorimetric applications remain difficult to develop, but a wide variety of chemical and biological analytes can still be detected qualitatively. These include HIV, tuberculosis, water-borne pathogens, environmental mercury contaminants, chlorine concentrations, and trace quantities of explosive materials.

Smart phone image processing methods are being developed for the detection and quantification of a wide range of targets, employing methods from microscopy to fluorescence techniques. However, most of the lab-based biological and biochemical assays still lack a robust and repeatable smart phone analogue. Existing solutions require external smartphone hardware to obtain quantitative results, imposing a design tradeoff between accessibility and accuracy.

Smartphones could be a viable healthcare solution for existing bulky laboratory equipment in the developing world because they can allow untrained users to collect data for transmission to medical professionals. Cell phone image processing can be accessible, user-friendly, and equipment-free. However, in practice cell phone image processing has limitations that severely restrict their utility. Cell phone cameras automatically perform a variety of preprocessing steps, including demosaicing, gamma correction, sharpening, and lossy image compression. These approaches are optimized for image appearance rather than for quantitative image-based measurements and cannot be bypassed or reversed easily.

Smartphone cameras capture the image as a set of red, green, and blue (RGB) image channels, which must be processed to obtain a single output measurement. Regardless of the analyte, most analysis methods compute the mean pixel intensity (MPI) of the RGB channels within a region of interest (ROI) in the image. Some processing methods use colorspace transformation, while others use the RGB averages or function of RGB values. In either case, the analysis depends on the existence of a relationship between RGB values and the concentration of an analyte. The method has shown good agreement with the absorbance readings from a visible-light spectrophotometer and is therefore useful for a wide range of bioanalytic applications. Linear regression models have been used to calibrate the mean pixel intensity response to an absorbance curve, with acceptable results under controlled conditions. The regression model must have a sufficiently high correlation and low standard error in the target range for the mean pixel intensity method to detect the target.

Unfortunately, imaging conditions can dramatically affect the validity of the analysis. If the image is taken at the wrong angle or the subject is out of focus, the analysis may fail. A variety of factors can interfere with the relationship between mean pixel intensity values and the target. In some cases, the relationship may completely disappear. The readout can be compromised by reflections and glare, the separation distance and angle between the camera and sample, ambient light variations, the size of the ROI, and even the location of the ROI in the image. Since smartphone cameras are optimized for consumer applications rather than scientific imaging, they apply automatic focusing and white-balance algorithms that complicate the problem.

This issue has been addressed using smartphone attachments. Such attachments provide constant illumination, standardize image capture conditions, and significantly improve the characteristics of the image. With high-quality input data, image processing can achieve repeatable results and low limits of detection (LOD). Although attachment-free methods are more accessible and cost-effective, external equipment is often needed to meet performance specifications because equipment-free methods suffer from repeatability and standardization problems. To contend with methods that rely on hardware, they require advanced processing methods that are robust to image capture conditions and can handle low-quality input data.

Recent efforts have focused on the measurement challenges associated with equipment-free imaging. It is desirable to eliminate the lighting box or attachment and replace it with better analysis methods, if possible. While lighting boxes and smartphone attachments are low-cost, they tend to be bulky, fragile and difficult to transport. Therefore, there has been a search for output metrics that are reliable under a wide variety of image capture conditions. The ROI median has been explored as an alternative to the MPI, as it is completely immune to limited amounts of discoloration. MPI ratio metrics are extensively used to achieve a form of standardization between different imaging environments, and colorspace transformation has yielded good results for color-change assays. The International Commission on Illumination (also known as the Commission Internationale de l'Elcairage (CIE)) 1931 chromaticity space, HSV hue channel, HSV saturation channel and grayscale intensity have all been used as alternative metrics. These methods work because they combine the raw RGB values in ways that decouple the MPI from interfering factors. Preprocessing operations have also been developed to reduce the effect of certain factors. For instance, a Fourier bias correction method can remove the effect of uneven illumination at the expense of MPI dynamic range.

However, performance is still dependent on a variety of factors whose effects cannot be completely removed from single images using algorithms. Undesirable interference due to experimental conditions can cause snapshot-based results to be unpredictable. This factor has been identified as one of the most fundamental challenges for smartphone image-based colorimetric measurements. Lighting boxes and smartphone attachments are indispensable because they remove detrimental factors from the algorithm input. However, the fact that specific problematic factors have been identified suggests that it may be possible to reliably differentiate between images that contain useful data and those that do not, even when a lighting box is not used. Given a large set of images, a classification selection approach via a set of rules could act as a virtual light box and select the best inputs for the processing steps, improving the quality of results when specialized equipment is not available. More importantly, this method could reject images with bad capture conditions. Such a method would also be able to provide users with instant feedback on the measurement, allowing them to improve conditions if needed.

Smartphone videos have not been considered for this purpose, even though they offer the ability to collect a large set of high-resolution images. Smartphone videos have been used to measure the rate of a chemical reaction, but have not been applied to tests that require a single measurement. However, video image data includes temporal information about imaging conditions, allowing time-dependent variations to be identified even for single endpoint measurements. Furthermore, analysis of a large collection of images may be more accurate than the unpredictable results of single image analysis.

Exemplary embodiments depict a cell phone or smartphone imaging approach that enables analysis of assays that would typically be evaluated via spectroscopy. The developed technique may use the saturation parameter of hue-saturation-value colorpace to enable point-of-care diagnosis in the field. Through the analysis of over 10,000 images the exemplary saturation method consistently outperforms existing methods under a wide range of operating field conditions. The exemplary approaches presented here are a step forward towards the development of point-of-care diagnostics by reducing the required equipment, improving the limit of detection (LOD), and increasing the precision of quantitative results.

An exemplary method captures smartphone video and obtains a best possible set of input data. The method tracks the correlation and standard error of a typical calibration dataset over several thousand video frames and examines factors that influence performance. In addition, the method identifies problematic image capture conditions. The method adds a classification approach that rejects low-quality input frames and may halve the limit of detection of bulky laboratory equipment of an assay, for example, an enzyme-linked immunosorbent assay such as a NS1-based Zika sandwich ELISA.

Figure 1:
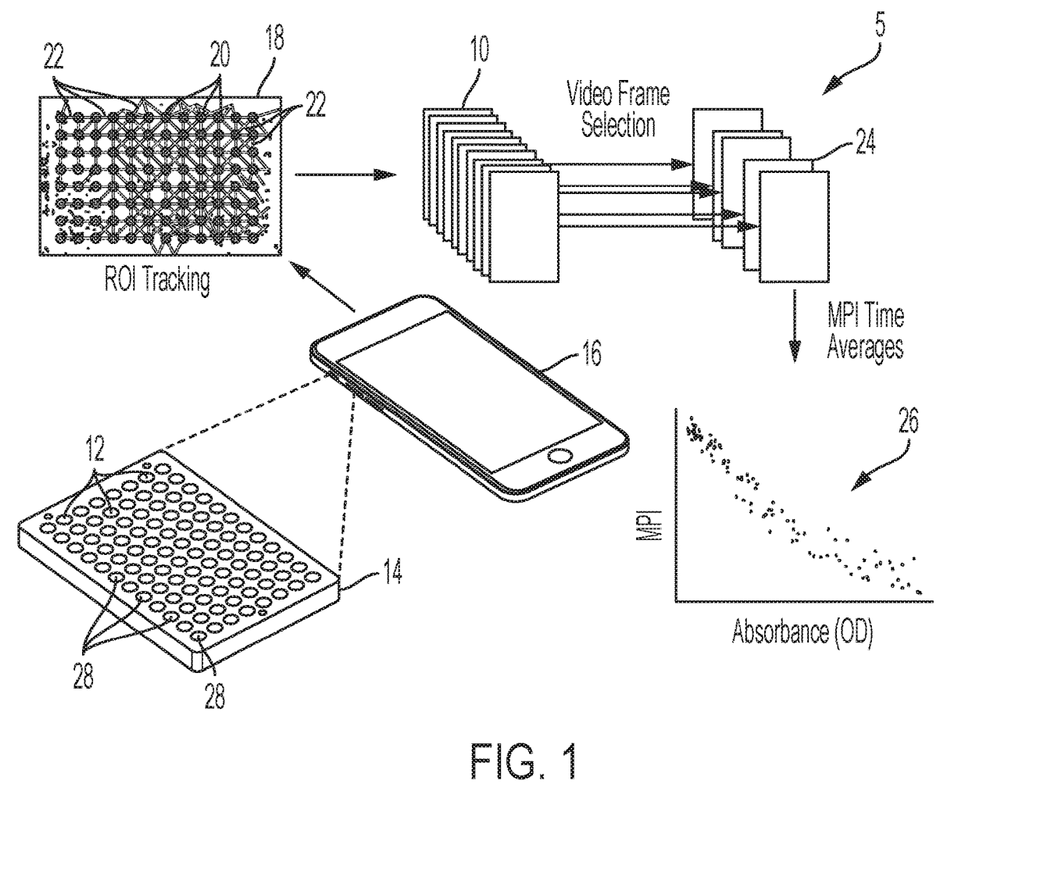
FIG. 1 illustrates an exemplary image processing system in accordance with examples of the embodiments.

FIG. 1 depicts an exemplary image processing system 5 illustrating an exemplary approach the equipment-free video method. Video frames 10 of an analyte sample 12 contained in a housing (e.g., well plate 14) may be captured by a smartphone 16 above the housing, here by example a 96 well plate 14. The video frames are stored in smartphone 16 memory as a video having a plurality of frames 10. For example, a video may include a plurality of frames of images per second, (e.g., at least 24 frames/sec, 60 frames/sec, 72 frames/sec). Video images in the video frames may be recorded by a smartphone 16 under different conditions. For example, video may be taken at different distances and angles, including angles ranging from 90 degrees (e.g., above the sample) to side angles such as about 45 degrees to the side of the sample, or lower. For optimal video quality, the video may be taken at a high resolution, such as an ultra-high 4K resolution (e.g., 5448×3264). Some images may be blurred, for example, if taken under sub-optimal conditions including high humidity or windy conditions, or when the camera is focused to an area away from the well plate.

Image data from the video frames 10 includes region of interest (ROI) data from the captured well plate 14 wells 28, which is extracted from the image data. In examples, each region of interest may correspond to a respective well.

The smartphone 16 may track image features within the region of interest data from the video frames throughout the video, for example via tracking instructions executed by the smartphone. In examples, the tracking instructions include region of interest tracking instructions to follow the wells 28 throughout the video. Based on the image features within each frame, the video frames are classified based on the quality of the image features, and the highest quality video frames 24 are selected for further processing. For example, selected video frame 24 image features may be processed via a MPI method, where the smartphone 16 computes the mean pixel intensity (MPI) of RGB channels within a region of interest (ROI) in the image. If desired, MPI analysis 26 may include time averages of the MPIs from the selected frames may be correlated with the absorbance.

While regions of interest may be manually tagged on a computer (one ROI per well), by a skilled user in about a minute, it is far too labor intensive and impractical to manually extract ROIs from each frame of a video. For example, only a 10 second video at 60 FPS will have 600 frames, requiring over ten hours of uninterrupted manual data entry. Likewise, automatic ROI extraction may be too expensive to compute for each frame on the smartphone. Therefore, the inventors developed an approach to extract and track ROIs from frame to frame throughout a video, given a set of initial coordinates.

For video extraction and tracking, the examples apply corner detection (e.g., Shi-Tomasi) to obtain a set of corner points for each ROI, and then determine optical flow (e.g., Lucas-Kanade) for each corner point. The term "corner points" refers to a set of points in each region of interest that may be tracked between frames of a video. In examples, the corner points may correspond to corners of the well plate and boundaries of each well. This correspondence to corners of a well plate 14 and boundaries of the wells 28 is not necessary as the corner points may refer to other easily tracked points determined by a point detection analysis, such as Shi-Tomasi, Harris, Plessy, or Laplacian algorithms.

In examples, the smartphone via instructions from the computer application updates the location of the ROI centers in each video frame under examination. Locations of the ROI centers may be determined using the detected corner points (e.g., 5 nearest corner points, 10 nearest corner points, a number of nearest corner points) with the shortest distance to the ROI center. In FIG. 1, an image frame 18 has ROI centers 20 influenced by the nearest 10 corner points to each center, with the corner points corresponding to boundaries of the wells 28. The image frame 18 is also shown with white lines 22 that show the influence of detected corner points to the centers 20.

Using the sparse optical flow of the image, the smartphone determines the distance each corner point had traveled since the previous frame, and moves the ROI centers 20 by the mean displacement of the ten nearest corner points to ensure that there was no drift and that the approach correctly extracts the 96 wells 24 for all video frames 10. Using a computer vision library (e.g., OpenCV), the video may be overlaid based on the ROI centers 20 to ensure that there is no drift and confirm that the approach correctly extracted the wells 28 for the video frames 10. OpenCV, a cross-platform computer vision library, may be used to implement the cell phone image processing approach because the same library is available for the Windows, OS X, Linux, iOS, and Android operating systems. This allows the app to be used for the most common types of POC smartphone-enabled systems, both on the cell phone device and on a remote server.

After image tracking, the system may better identify and reject video frames having problematic images thereon. The inventors designed image features that may be used to identify and reject problematic images, such as blurred images, images with excessive white-balancing, and images that may have other issues including glare and reflection.

The system rejects images having regions of interests (ROIs) out of focus because signals indicating the light intensities in the red, green, and blue image channels from adjacent ROIs can overlap in a blurry image. Blurred images pose problems for ROI extraction and for ROI tracking. Problematic images can be identified, for example, using the variance of the Laplacian of the image, referred to as the Laplacian blur metric (LBM). If the image has no sharp edges and is out of focus, then the Laplacian blur metric will be low (e.g., LBM<10). Higher Laplacian blur metric values indicate a sharper image. The smartphone 16 computer programmed microprocessor may be instructed to compute this feature only for the ROI areas of the image occupied by the well plate. Other undesirable parts of the image in an image frame 18 may be in focus even when the ROIs are not, artificially raising the variance of the Laplacian.

The smartphone 16 computer programmed microprocessor may detect images with glare, reflections, or suboptimal ROIs via consideration of pixel intensity variance of the ROIs. Glare and reflections can cause part of a ROI to be discolored and have abnormally high intensity, while off-center ROIs contain pixels from regions of the image that should not be measured. Images taken at an oblique angle often include undesirable refractions from edges of the well plate 14. Glare and reflections from a ROI introduce multimodality, increase the range of pixel values, and artificially shift the mean pixel intensity (MPI) value. These features will therefore increase the variance of the pixel intensity histogram within the ROI. The inventors determined the maximum variance threshold of ROIs in a frame. This may be determined, for example, by computing the variance of the pixel intensities for each ROI in the frame, and then selecting the largest variance over the ROIs as the maximum variance.

Automatic white-balancing of smartphone videos and pictures causes a vertical shift in pixel intensity values, making it difficult to compare MPI values from image to image. Images that are improperly white balanced require bias correction and the results suffer from a reduced dynamic range. Image burning effects, where the image appears washed-out and the dynamic range is affected, may also result from glare and improper white balance conditions. To detect issues with white balancing, the smartphone 16 computer programmed microprocessor determines the first difference of the blue MPI over time. If the MPI values in a frame change significantly from a previous frame, then magnitude of the first difference is large.

As an exemplary approach to identify and reject video frames having problematic images thereon, the smartphone captured images and videos of an Anti-HIV-1 p24 dataset under diffuse indoor lighting provided by white fluorescent overhead lights. The smartphone 16 computer programmed microprocessor analyzed the images with the MPI of the RGB blue image channel. This value is computed as the arithmetic mean of all pixel intensities in the blue channel of the ROI. MPI and absorbance have an established linear relationship for sufficiently small absorbance values (OD<1), which is also the most common absorbance range for bioanalytic applications. The smartphone 16 computer programmed microprocessor also computed the image features for each frame to investigate relationships between the features and quality of the calibration data. The smartphone 16 computer programmed microprocessor rejected frames with a low blur metric (LBM<10) and high ROI variance to obtain a high-quality subset of the video frames. The blur threshold was found by noting the point at which manual ROI identification became difficult. For the variance threshold, the smartphone 16 computer programmed microprocessor rejected frames with a value greater than 25% of the maximum variance in the entire video. The smartphone 16 computer programmed microprocessor found 96 MPI time averages by computing the mean of the MPI values from all selected frames. Since the sample sizes of each ROI were the same, the time average is equivalent to the grand mean of all pixel values within the ROI for every frame. The smartphone 16 computer programmed microprocessor also found the 96 ROI time averages for the entire video, for comparison and to determine whether frame averages can improve performance.

In addition to the fluorescent overhead lighting in the lab, images and videos were also captured by the smartphone 16 outdoors under completely uncontrollable imaging conditions. No external equipment was used, and images and videos were captured under a wide range of image capture conditions. The inventors found that imaging conditions to analyze the colorimetric assays can vary even over the course of a few seconds of video, adversely affecting our MPI analysis. The inventors observed an improvement in performance when using the average from multiple frames, with an additional improvement from our frame selection process.

Figure 2:
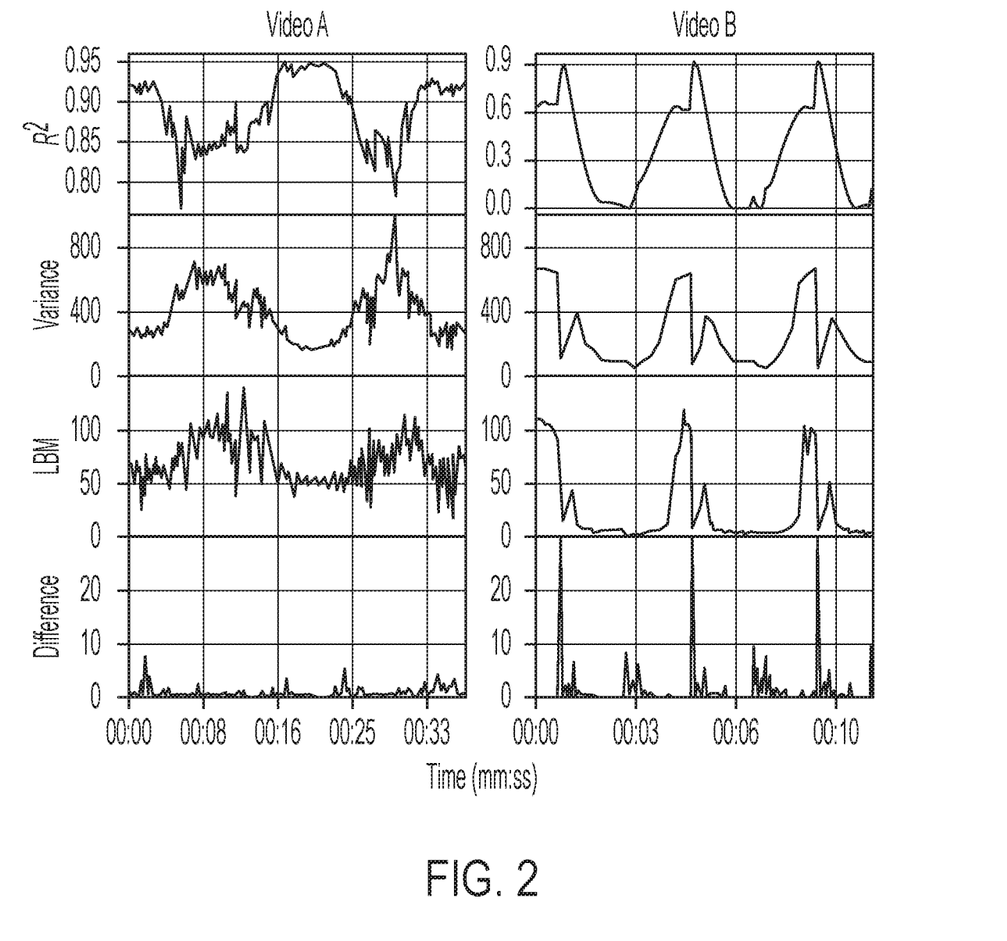
FIG. 2 a plot of image features and mean pixel intensity parameters over time.

FIG. 2 shows a plot of our image features and the MPI analysis parameters over time. Exemplary video A was imaged at a variable distance to the liquid sample without interference. The minimum separation distance was reached at 00:09 and 00:27, while the maximum distance was reached at 00:18. Exemplary video B was subjected to automatic white balance and blur at 00:01, 00:05, and 00:09. The inventors induced these effects by refocusing the camera away from the 96 well plate after one, five, and nine seconds of video. For the first 16 seconds of video A, the camera was moved vertically toward and away from the plate. The remainder of video A was taken under approximately constant conditions.

In both videos, changes in variance and LBM were associated with changes in the correlation coefficient. The ROI variance increased within the majority of the wells 28 for substandard imaging conditions. The first difference also had a relationship with the predicted video characteristic, with peaks that aligned with the white-balance and blur events in video B. Such events were not present in video A, where the first difference had a relatively small absolute value. Dynamic range was also an important difference between video A and video B. The frames with the highest correlation in video A had an MPI range of 60, while the highest correlated frames from video B had an MPI range of 45.

Figure 3:
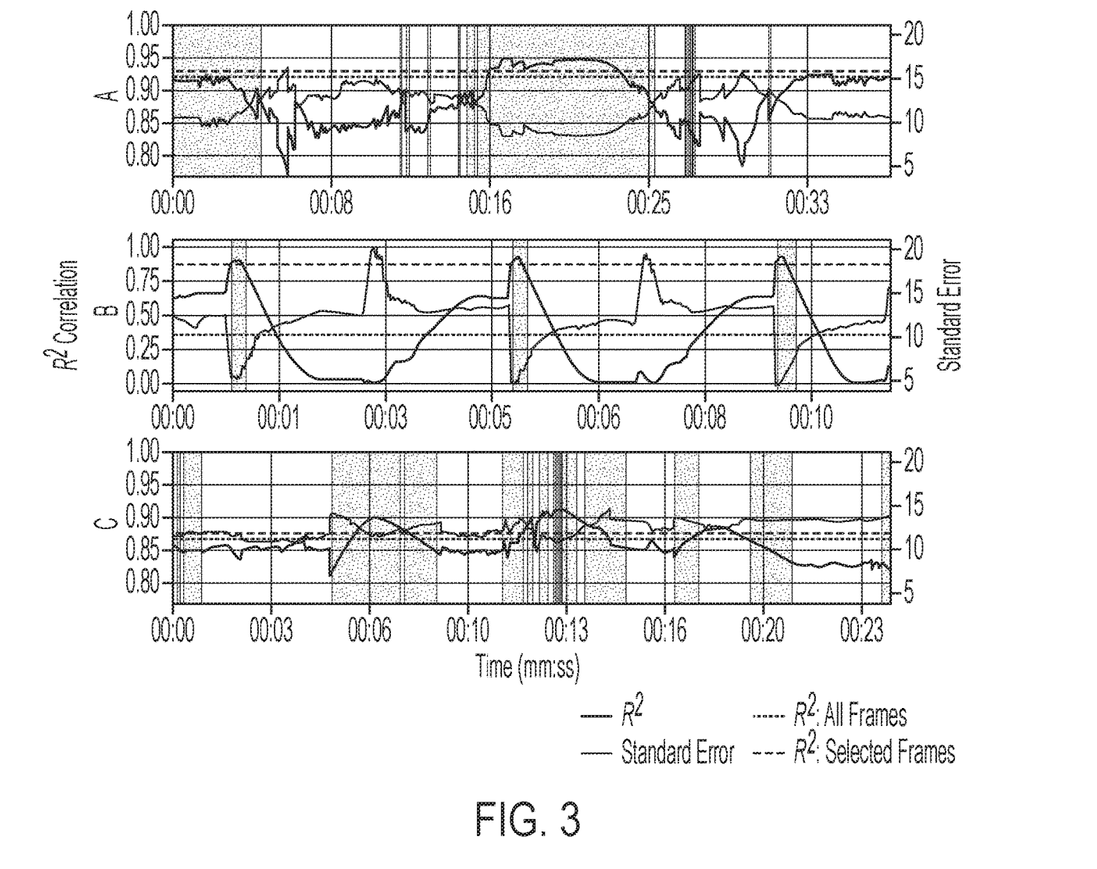
FIG. 3 illustrates frame classification results for three exemplary videos captured by smartphone.

FIG. 3 illustrates frame classification results for three exemplary videos A, B and C. Video A (top) was imaged with a variable distance to the sample. Video B (middle) was subjected to blur and white balance modifications. Video C (bottom), taken with an off-center 96 well plate, introduced a horizontal displacement at 00:10 and 00:21 causing the 96 well plate to be off center. Shaded regions of the plot indicate frames that were selected by the classification process, where the video frames are classified based on the quality of the image features, and the highest quality video frames selected and available for further processing as desired. The dashed line indicates the R2 of the time-averaged MPI from the selected frames. The dotted line indicates the R2 of all frames in the entire video. In video A, selected frames (n=1225) had an average $R^2$ of 0.93 (s=0.02) while rejected frames (n=1038) had an average $R^2$ of 0.85 (s=0.03). For video B, acceptances (n=50) had an average $R^2$ of 0.87 (s=0.05) while the rejections (n=623) had an average $R^2$ of 0.31 (s=0.26).

The inventors found that the correlation, standard error, and range of the response are directly affected by factors during image capture, even for images that are taken under similar conditions and look the same. Since these parameters are directly related to the LOD and quantification performance, MPI analysis suffers from repeatability and standardization issues. In some cases, the correlation between absorbance value OD and MPI can drop to minimal levels and the range of the response can vary, for example, by a factor of two. Performance problems can be caused by changes in experimental conditions including background light intensity, distance from the phone to the sample, position of the camera, and camera settings such as white balance and blur. It is beneficial to center the image on the sample and the ROIs in the wells 28 of the well plate 14. Single snapshot images can be unreliable even when taken under the same environmental conditions with camera position, settings, and angle held constant.

Using these features, the classification method can detect and reject conditions that interfere with the optical density measurement. The feature-based method does not require prior knowledge of a calibration result or spectrophotometer readout. The method enables image capture applications that provide immediate user feedback during data collection and that automatically detect when a good measurement can be made. The use of high-quality input data results in an increase in the correlation of the calibration curve and a reduction in standard error. The classifier improves the measurement process because it rejects snapshots that are likely to produce outliers, leaving non-rejected video frames selected. The selected video frames may be output for analyte imaging time-averaged mean pixel intensity analysis. The selected frames may be output to data storage accessible from the smartphone or another computer for later processing or output directly to a data processing algorithm for immediate processing. The selected video frames in this example include region of interest data processed via the selection as the highest quality region of interest data. The processed region of interest data may then be quantified for MPI analysis, as discussed in greater detail below.

Video methods are not currently prevalent in the literature, but they merit further exploration for bioanalytical applications because they may offer a wealth of information about imaging conditions. The exemplary classification method exploits this information to filter out variations in image capture conditions from the input data. Since the frame selection method acts as a preprocessing technique, it can be used with any existing processing approach. Although the most common forms of MPI analysis were used, the classifier output could have been fed into systems that perform colorspace transformation, correct white balance, standardize ambient lighting variations, or use calibration strips. Regardless of the processing technique, high-quality inputs will improve the characteristics of the output. By imposing restrictions on video frame quality, our approach selects the best possible set of input images and acts as a more portable improvement over current smartphone point-of-care attachments.

The exemplary method is generally applicable to any smartphone imaging method that uses an output parameter to estimate a colorimetric change. The developed video method is easy to integrate with other processing techniques, since it acts as a preprocessing and post-processing step. Existing approaches can be applied to each frame and used to obtain the output value without any modification. The video analysis can improve measurement performance for a wide range of POC tests and lead to more user-friendly measurement applications. An exemplary user-friendly measurement application is analyzing intensity change assays.

As discussed above, smartphones have emerged as highly capable evaluation tools at the point-of-care (POC) for a wide range of applications, including smartphone microscopy, cytometric analysis, lateral flow assays, paper-based microfluidic devices, and colorimetric tests. Smartphones including mobile cell phones are an attractive option because they combine sophisticated onboard sensors, powerful processing capability, and wireless connectivity into a portable device. Distributed smartphone sensing networks can generate spatiotemporal maps of measurement results, providing information for epidemiology studies, environmental monitoring, and other applications where real-time measurements are critical. Self-contained smartphone applications, which solely use the cell phone processor, have been reported and are capable of providing a readout for biomedical assays in remote locations, where communication with offsite computer systems and medical professionals may be unavailable. In particular, camera technology has improved at an exponential rate, and the camera sensor has been used to obtain useful quantitative and semi-quantitative measurements with low limits-of-detection (LOD) for fluorescent and non-fluorescent assays. Smartphone image processing has been applied for analytes including the human immunodeficiency virus (HIV) p24 capsid protein, tuberculosis DNA, mercury and chlorine contaminants, glucose and protein concentration in urine, ovarian cancer antigens, and water-borne pathogens. As a result, some mobile phone-based methods inherently involve some form of smartphone image processing, which is consequentially becoming an important technological field.

The most convenient color space for cell phone image processing is the red-green-blue (RGB) color space, because cell phone images are natively stored as arrays of RGB pixel intensities, commonly referred to as color channels. Unfortunately, as discussed above, RGB values are highly susceptible to ambient lighting noise, including when the illumination varies between different regions of the image. This problem is most commonly mitigated through the introduction of external smartphone attachments[9]. These attachments include LEDs with optical diffusers to provide constant illumination, an imaging chamber to block ambient light variations, rigid components to hold the phone in place, and optical filters or lenses.

Software-based strategies to combat the adverse effects of unpredictable image capture conditions are mainly used in conjunction with external imaging equipment and attachments. An improvement for determining best images from a video of images without external imaging equipment and attachments is discussed above.

The parameter used to quantify analytes, or the output metric, is often a function of the arithmetic mean pixel intensity (MPI) inside a region-of-interest (ROI) for one or more of the RGB image channels. The MPI of an individual RGB channel has been successfully used directly as the output metric, but alternative approaches can improve system performance. A common alternative is to use a ratio of RGB channel MPIs, referred to as RGB ratio tests. Principal component analysis has been used, but this method is application-specific and has not been used for quantification. Instead, color space transformation has proven to be a very effective, simple, and general method for quantitative colorimetric analysis. In color space transformation analysis, RGB values are transformed to an alternative set of coordinates before MPI analysis is performed. The standardized CIE 1931 chromaticity space has enabled quantification of protein and glucose without any imaging equipment, but is only sensitive to changes in color. Assays that respond with a chromatic intensity change but no wavelength shift cannot be analyzed using these methods. Assays that would normally use absorbance spectroscopy are currently limited to noise-sensitive RGB analysis and RGB ratio tests at the point-of-care.

Here, in accordance with aspects of the invention an exemplary color space transform technique may analyze intensity change assays with significant improved precision when compared to existing RGB-based methods. This approach transforms images to hue-saturation-value (HSV) space and uses the MPI of the saturation channel as the output metric. HSV space refers to a well-established cylindrical-coordinate representation of RGB space, with an invertible transformation from RGB to HSV coordinates. In HSV space, the hue channel corresponds to the color or wavelength of the sample, the saturation channel corresponds to the chromatic intensity, and the value channel is a measure of the overall light intensity. Saturation channel has never been used before to provide readout for absorbance spectroscopy or colorimetric tests. Common teachings have not suggested that nonlinear colorspace transformation using saturation as a de-noising approach enabling equipment-free imaging improves the signal when compared to R,G,B or (linear) PCA components. Known literature uses a light box as a smartphone attachment, and the common wisdom is that you cannot get good results without smartphone attachments. Yet the inventors found that under conditions present in most assays, saturation is an alternative to the most optimal RGB ratio test for a given sample. The inventors also found that saturation is not sensitive to ambient lighting conditions, and that saturation values may be tracked and processed over sets of video frames. Further, the examples use saturation to determine absorbance values in addition to analyte concentrations, which allows analysis of a greater number of assays more efficiently at the point of care.

The inventors address the issue of repeatability for cell phone based colorimetric tests by processing approximately 10,000 ROI images taken under a range of image capture conditions. These images include photos taken under a range of ambient light levels, against a variety of backgrounds, with and without external imaging equipment, and with three separate cell phone cameras. The inventors found that changes in ambient light intensity are reflected in all three RGB channels but are present only in the mean and standard deviation of the HSV value channel, leading to an improved repeatability when HSV space is used. For example, the inventors applied saturation MPI analysis to a direct ELISA for the HIV p24 capsid protein and found that the saturation parameter of HSV space can enable an equipment-free evaluation for p24 antigen.

OpenCV, a cross-platform computer vision library, was used to implement the cell phone image processing approach because the same library is available for the Windows, OS X, Linux, iOS, and Android operating systems. This allows the app to be used for the two main types of POC smartphone-enabled systems, both on the cell phone device and on a remote server. As a proof-of-concept, an Android application was written to show that saturation computations for a typical ROI are computationally within range of low-end smartphone processors. However, for data collection purposes, a semi-automated application was written for desktop systems that processes cell phone images.

Figure 4:
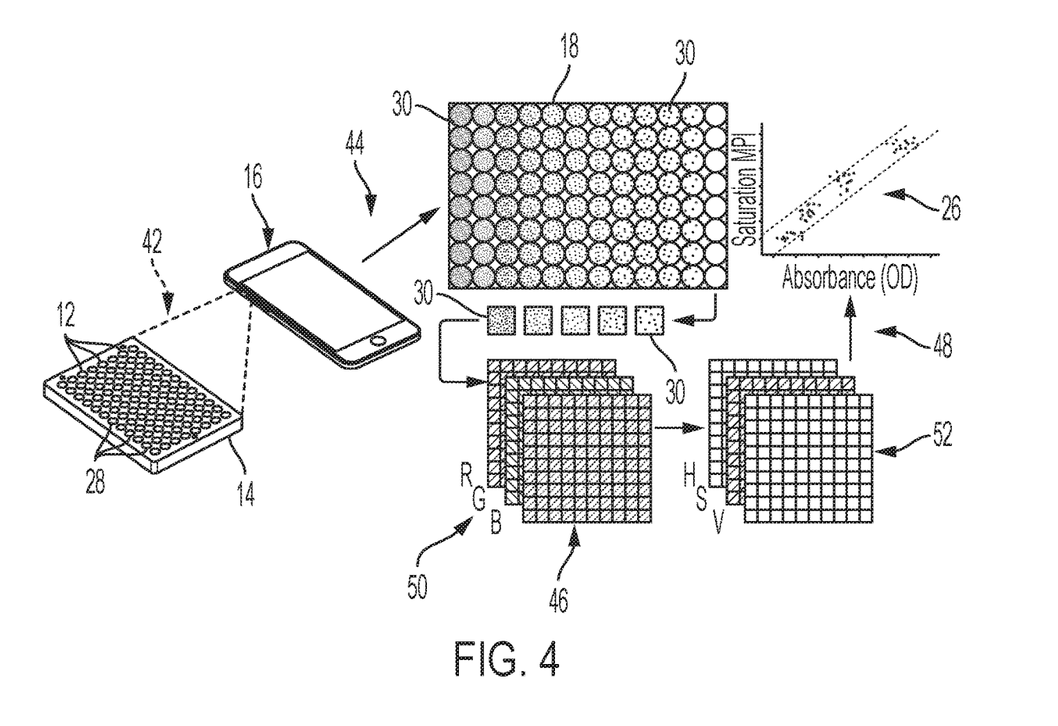
FIG. 4 illustrates another exemplary image processing system in accordance with examples of the embodiments.

FIG. 4 depicts another exemplary image processing system 40 including four components: image capture 42, ROI extraction 44, ROI processing 46, and quantification 48. An image capture phase includes the smartphone 14 reading CMOS camera sensor data (e.g., at least one video frame 10 of analyte sample 12 contained in well plate 14), which is handled by the processor, operating system and memory of the smartphone. At this stage, unavoidable preprocessing steps including demosaicing, sharpening, gamma correction, JPEG compression, and white balancing may occur. ROI extraction 44 is discussed by example above, and may include extracting image data from regions of interest of the captured well plate 14, and tracking the image data across multiple video frames where the image capture 42 includes a plurality of frames. Video data from the video frames 10 includes region of interest (ROI 30) data (e.g., RGB data) from the captured well plate 14 wells 28, which is extracted from the image data. The extraction thus removes portions of the image that are not relevant to the test and distinguishes between multiple samples if they are present.

After the regions of interest are extracted, the ROIs 30 may be converted from RGB space 50 to hue-saturation-value (HSV) space 52 during ROI processing 46. Quantification occurs when some characteristic of a processed ROI 30 is used to estimate a physical quantity. In examples after the conversion to HSV space 52, a standard MPI analysis 26 may be applied to the saturation channel and the values used to determine absorbance and concentration of the sample, as understood by a skilled artisan. ROI processing 46 may also include color-space transformations, image filtering, thresholding and morphology, and other image processing steps. In examples, the system uses image-based measurements to estimate absorbance readings from a spectrophotometer and hence protein concentrations measured by a direct ELISA.

As discussed above, image capture 42 may be conducted using smartphones 16. While not being limited to any particular smartphone or mobile phone, some exemplary smartphones 16 may include a smartphone having a camera with at least 3 megapixels, including an Android Moto with a 5 megapixel (MP) camera, an iPhone with a 12 MP camera, and a Samsung Galaxy with a 12 MP camera. To facilitate data collection, the inventors developed a desktop GUI application using Python and OpenCV that may be used to enable manual ROI extraction. Such methods typically involve imaging a small number of samples at a time, which is the equivalent of extracting fewer ROIs 30 with the desktop application. Of course ROI extraction 44 may be automatic, which is essential for video files greater than several seconds with manual extraction of many thousands of ROIs 30 manually impractical, as discussed in examples above. This process enables the collection of large amounts of data, by allowing all ROIs 30 to be isolated in a 96 well plate 14 with the ROIs extracted automatically by the programmed smartphone 16, for example as discussed above. This may also enable meaningful comparisons between samples 12 in a well plate 14, since image capture conditions are approximately the same for all ROIs 30 of a source image.

The saturation analysis is part of the exemplary ROI processing 46 and is not dependent on the type of ROI extraction 44, provided that the extraction is adequate. The exemplary ROI processing 46 includes transforming the RGB coordinates to HSV color space and computing the MPI, which is the arithmetic mean of pixel intensities, in the saturation color channel. The MPI values are then used to quantify the biological analyte. RGB coordinates can be transformed to normalized HSV space via Equations 1-3. We used the non-normalized HSV space, which simply requires multiplication by 256. Equation 3 shows the process to obtain the MPI of channel $\alpha$, denoted as $\alpha_{MPI}$.

$$S = \frac{\max(R, G, B) - \min(R, G, B)}{\max(R, G, B)} \quad (1)$$

$$H = \begin{cases} 60\left[\frac{G-B}{\max(R,G,B)-\min(R,G,B)}\right] \bmod(6) & \max(R,G,B) = R \\ 60\left[\frac{B-R}{\max(R,G,B)-\min(R,G,B)} + 2\right] & \max(R,G,B) = G \\ 60\left[\frac{R-G}{\max(R,G,B)-\min(R,G,B)} + 4\right] & \max(R,G,B) = B \end{cases} \quad (2)$$

$$V = \max(R, G, B) \quad (3)$$

$$\alpha_{MPI} = \frac{1}{N}\sum_{n=0}^{N} \alpha_n \quad (4)$$

If image-based metrics have a strong relationship with laboratory measurements, and the laboratory measurements are an accurate predictor of biological analytes, then the image metrics will also measure the biological analytes, albeit with a larger standard error. Image-based metrics may represent biological values, such as protein concentrations. To show how MPI values compare to absorbance values (OD) and to each other, the inventors compared summary of the output values vs. concentration. This shows the variance of the MPI response and provides a way to compute the instrument LOD, or the magnitude of MPI response that is significant at low concentrations.

The pixel intensity distribution within the ROI should be Gaussian or at least unimodal with low skewness. In practice, this results in outliers that increase the mean-squared error of the linear regression model and the variance within each concentration category. This requirement may be verified by comparing the image pixel intensity histograms for RGB and HSV channels and ensuring that most ROIs 30 did not have a significant departure from normality.

To validate the exemplary approach, HSV analysis was applied to quantify a direct ELISA for HIV-1 p24 antigen. The p24 antigen is the capsid protein that forms the structural virion component of HIV. It is widely used targeted in several HIV-1/-2/-O ELISA diagnostic kits using colorimetric quantification, and serves as means to detect HIV viremia, as it is present in early stages of infection. The diagnostic window is shortened, with detection found prior to anti-body seroconversion, when HIV antibodies are detectable. This comprehensive approach using combined antigen/anti-HIV antibody detection, leveraged with rapid point-of-care diagnostic platforms is further enhanced using cell phone absorbance quantification, and could potentially be used to detect a multitude of different pathogens or diseases. For anti-p24 HIV direct ELISA curve (Supplementary Materials, Assay Protocol 2), images were taken for a variety of image capture conditions, including variable light level, presence and absence of an image box, variable distance to the sample, and variable background color. This data corresponds to absorbance values in the linear response range for MPI analysis.

In examples, the saturation channel of the processed ROI data is quantified to determine absorbance and concentration of the analyte sample. The saturation channel may be quantified by computing a statistical measure of the ROI data from either a single image or a set of video frames. While the mean is used, it us understood that one can also use the median, the median-of-means, or related estimators. To determine the absorbance from the saturation value, the inventors created a single-variable linear regression model going from saturation to absorbance. This model may also include multiple features from different video frames (in the case of video). This model indicates the absorbance value most likely to cause a given saturation measurement.

To determine the concentration of an analyte sample, another model for saturation vs concentration may be created and used, as well understood by a skilled artisan. This is a common workflow, but another approach may be preferred. In examples, assays are provided with standard curves, which relate absorbance to concentration. Absorbance values have already been estimated and may be used directly into a standard curve for that assay as understood by a skilled artisan.

The saturation method may be applied to a calibration dataset from a standard dilution and to a direct ELISA for the HIV p24 protein. For the calibration dataset, scatterplots may be generated for the set of ROIs in each image with a variety of smartphones and image capture conditions. While not being limited to a particular theory, in image sets, each image shown is of a 96 well plate and contains a number of sample ROIs 30, each of which has an absorbance value measured via spectrophotometer and an MPI value measured via smartphone camera. From this, the Pearson product moment correlation between absorbance and MPI may be determined.

The inventors found that there is a strong relationship between absorbance values (OD) and MPI. A logarithmic model provides the best prediction over a wide optical density range with high r-squared correlation ($r^2 > 0.98$), and there is a linear region in the MPI response from 0.2 OD to 2.0 OD. The scatterplots also reveal that some of the RGB information is redundant, since each color channel MPI shows a response to changes in absorbance. Even though all the RGB channels respond, RGB analysis is typically done only with the channel with the largest dynamic range. In this example, the blue MPI had the largest dynamic range and was therefore chosen as the RGB metric. In HSV space, the hue parameter is constant, and the value parameter is approximately constant. Only the saturation parameter responds to changes in absorbance, and the dynamic range of saturation MPI is larger than the dynamic range of the blue MPI variation. In terms of the strength of correlation, the saturation MPI is not affected by ambient light and remains very strong ($r^2 > 0.9$) even under non-ideal smartphone image capture conditions.

Serial dilution examination of samples to determine how saturation and blue MPI values are affected shows that the slope and variance of the saturation response are more consistent than those of the blue response when images are taken outside the box. This indicates that saturation MPI is more consistent and a better metric than blue MPI under varying measurement conditions.

The histograms of each of the RGB channels were all similar in terms of variance and multimodality. We observed distributions for the RGB values that were mostly unimodal. The histogram of the hue channel had a very small variance which is constant inside and outside of the imaging box, explaining the success of colorimetric tests based on the chrominance signal. The saturation channel typically had a unimodal response that can be adequately described by the MPI. Finally, the value channel follows the distribution of the RGB channels, but is not related to the saturation evaluation steps. Since most of the RGB and HSV distributions are unimodal with low skewness, the simple MPI analysis was appropriate and the results are valid.

To illustrate performance improvement from saturation, the effect of additive noise on the RGB and HSV MPI values may be considered. Images are captured in the RGB format, so additive noise takes the form of a superimposed noise image that corrupts each pixel. Additive noise may be introduced by uneven illumination, shading, tilt and distances to the sample. If the sample is illuminated by diffuse, full spectrum white light, then the local ambient lighting variations will be approximately the same for each of the RGB channels. If $\delta_n$ represents the additive noise at pixel n with a mean of $\delta_{MPI}$, then the RGB MPI for the blue channel of a noisy image ($BN_{MPI}$) and the saturation channel of a noisy image ($SN_{MPI}$) are:

$$BN_{MPI} = \frac{1}{N} \sum_{n=0}^{N} B_n + \delta_n$$

$$BN_{MPI} = B_{MPI} + \delta_{MPI}$$

$$SN_{MPI} = \frac{1}{N} \sum_{n=0}^{N} \frac{\max(R_n, G_n, B_n) + \delta_n - \min(R_n, G_n, B_n) - \delta_n}{\max(R_n, G_n, B_n) + \delta_n}$$

$$SN_{MPI} = \frac{1}{N} \sum_{n=0}^{N} \left( \frac{\max(R_n, G_n, B_n) - \min(R_n, G_n, B_n)}{\max(R_n, G_n, B_n)} \right) \left( \frac{\max(R_n, G_n, B_n)}{\max(R_n, G_n, B_n) + \delta_n} \right)$$

$$SN_{MPI} = \frac{1}{N} \sum_{n=0}^{N} S_n \left( \frac{\max(R_n, G_n, B_n)}{\max(R_n, G_n, B_n) + \delta_n} \right)$$

If $\max(R_n, G_n, B_n) \gg \delta_n$, as is often the case, then the saturation MPI will not be affected by additive noise because the multiplicative distortion approaches unity. On the other hand, RGB MPIs add the mean of the noise to the output metric. Additive noise is present during image capture and can be due to diffraction, reflection, ambient lighting variations, and illumination by multiple sources of incoherent light. Regardless of the noise source, saturation MPI exhibits a reduced sensitivity to additive pixel intensity variations.

Saturation also has desirable characteristics when exposed to multiplicative noise, which occurs when the overall lighting level changes. This is the primary cause of differences between RGB MPI curves from different images, since image sets taken under similar conditions tend to have low variance. A lower overall light level compresses the entire curve, resulting in a downward shift. When an image is illuminated by white light and the intensity of the light changes due to shadows or large-scale changes in light intensity, the effect is multiplicative because low light levels result in pixel values close to zero, while bright light results in proportionally larger RGB values. For multiplicative noise where the light level changes by some value $\alpha_n$:

$$BN_{MPI} = \frac{1}{N} \sum_{n=0}^{N} \alpha_n B_n$$

$$SN_{MPI} = \frac{1}{N} \sum_{n=0}^{N} \frac{\alpha_n \max(R_n, G_n, B_n) - \alpha_n \min(R_n, G_n, B_n)}{\alpha_n \max(R_n, G_n, B_n)} = S_{MPI}$$

The saturation MPI is not affected by multiplicative noise and is therefore insensitive to the ambient light level. This enables equipment-free imaging because the ambient lighting level no longer has to be standardized to compare the output against a standard curve. This built-in pixel intensity normalization is not present for RGB analysis. The RGB response had a greatly reduced dynamic range and was much different from the response for ideal capture conditions.

Regarding saturations relationship with RGB ratio test, the absorbance changes while the color and wavelength do not. Hue is the hue-saturation-value (HSV) space analogue for wavelength, and it did not change in tests. In fact, when the hue in HSV space does not change, the maximum and minimum components of the RGB images always come from the same channels. Assuming that one of the color channels is maximum, Hue is a nonnegative quantity, and the denominator is always positive. Therefore, the minimum color channel is constrained because the numerator cannot be negative. For example, when red is maximized, blue must be the minimum so that G–B is nonnegative. This has practical implications for absorbance spectroscopy. Specifically, this leads to the result that saturation represents the most optimal RGB ratio test in this case. The saturation MPI can be written as:

$$S_{MPI} = \sum_{n=0}^{n=N} \frac{S_n}{N} = \sum_{n=0}^{n=N} \frac{1}{N}\left(1 - \frac{\min(R_n, G_n, B_n)}{\max(R_n, G_n, B_n)}\right)$$

$$S_{MPI} = 1 - \frac{1}{N}\sum_{n=0}^{n=N} \frac{\min(R_n, G_n, B_n)}{\max(R_n, G_n, B_n)}$$

If the wavelength does not vary, min(R,G,B) will always come from the same color channel, as will max(R,G,B). Therefore, saturation is fundamentally related to the particular RGB ratio with the greatest difference between numerator and denominator, and so there will be the largest possible variation in response. Therefore, the saturation MPI is an optimized RGB ratio test that maximizes the dynamic range and is adjusted to pass through the origin. Since the HSV color space transformation does not increase the variance of the MPI response except at very high concentrations, the saturation MPI is at least an alternative to the most optimal RGB ratio test.

The properties of the saturation MPI make it a good alternative to RGB-based output values for the analysis of colorimetric assays where the absorbance changes but the wavelength does not. For this set of assays, saturation is strongly related to the ratio tests commonly in use, but has reduced sensitivity to additive and multiplicative noise. Ambient lighting variations, which are commonly cited as the most problematic factor for equipment-free evaluation, have a greatly reduced effect on saturation, as shown by the correlation with absorbance and the variance. This causes the LOD of a saturation-based test to be lower than the one for an RGB-based test. Multiplicative noise and light level shifts are completely removed by saturation, which has important consequences for repeatability and practical POC systems. Since the ambient light level is no longer a factor affecting the readout, the intensity of the light source no longer needs to be controlled. Saturation analysis enables equipment-free evaluations, making POC applications more convenient and accessible.

Provided that the color does not change, the saturation MPI can be used for any color sample, since the inventors found that relating it to a RGB ratio test is valid for all hue values. However, saturation MPI analysis cannot be used for color change assays, as saturation does not contain chrominance information. Instead, the existing CIE or hue MPI method should be used.

The disclosed embodiments may include an exemplary smartphone based image processing method depicting the operation of an exemplary image processing system 5, 40.

Figure 5:
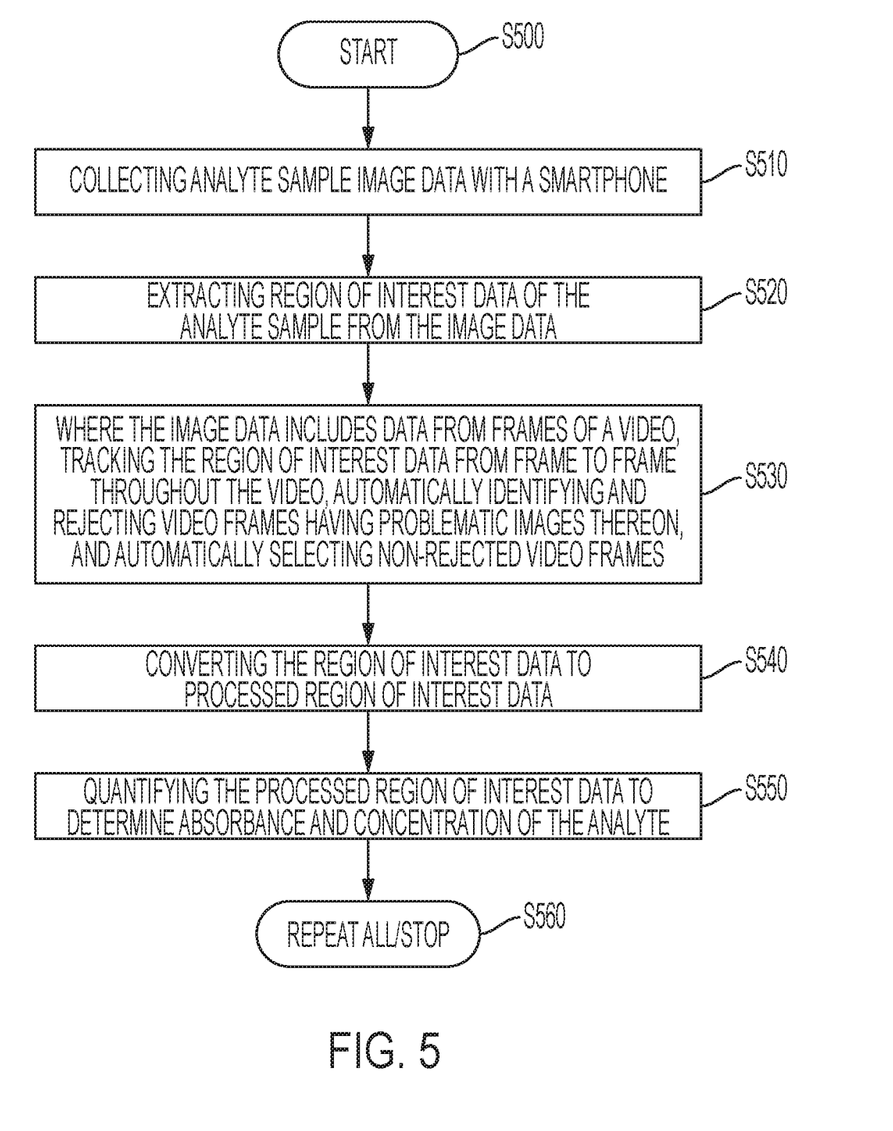
FIG. 5 is a flowchart depicting the operation of an exemplary image processing system.

The exemplary method commences at Step S500 and proceeds to Step S510. At Step S510, the smartphone collects analyte sample image data in the form of a single image frame or a video having a plurality of image frames. Operation of the method proceeds to Step S520, where region of interest (ROI) data from the image data is extracted from the image data. The ROI data may include red, green, and blue data In examples where the image data is from a video of the analyte sample, it may be desirable to use only the best video frames for analysis. Accordingly, at Step S530 the region of interest data is tracked from frame to frame throughout the video. Then video frames having problematic images thereon are rejected, leaving non-rejected video frames for selection by the smartphone.

Operation of the method illustrated in FIG. 5 proceeds to Step S540, where the region of interest data from the image date frame or selected video frame is converted to processed region of interest data. The processed region of interest data may include hue-saturation-value color space data having a saturation channel corresponding to the chromatic intensity of the region of interest data. Operation proceeds to Step S550, where the processed region of interest data is quantified to determine absorbance and concentration of the analyte sample. At Step S560 operation may repeat back to Step S510 to collects more analyte sample image data, or operation may cease upon completion of image date collection.

The exemplary cell phone based image processing method produces an MPI output with smaller variances, lower LODs, and a higher dynamic range than existing methods. Using several thousand images, the inventors compared saturation analysis with existing RGB methods and found both analytically and empirically that it has improved performance in the presence of additive and multiplicative ambient light noise. Saturation analysis can be interpreted as an optimized version of existing RGB ratio tests, and verified that the ideal image capture conditions include constant white light and a clean white background. When applied to an ELISA for the p24 HIV capsid protein, saturation analysis enabled an equipment-free test evaluation with an LOD two times lower than the one available with RGB methods. The saturation MPI represents an improvement in repeatability, practicality, and image capture noise rejection. Saturation analysis is not affected by many of the major limiting factors for image-based tests, such as ambient lighting variations, shading, and variable light levels. The favorable properties of saturation analysis will encourage and enable cell phone image-based POC tests with less equipment overhead and lower LODs.

The computer application instructing the smartphone 16 to carry out the exemplary method may be software, hardware, firmware, or some combination thereof. The application may be executed on a small computer, such as a smartphone as used in examples, and allows users access via a graphical user interface in communication with smartphone to control the video taking and image processing steps. The smartphone may include a microcontroller programmed via the computer application to carry out steps of the approach.

In an exemplary embodiment of the present invention a computer system may be included and/or operated within which a set of instructions, for causing the machine (e.g., cytometer, smartphone) to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. While the machine is discussed in the examples as a smartphone and cytometer, it is understood that the machine may be a personal computer (PC), a tablet PC, a set-top box (STB), a personal digital assistant (PDA), a cellular telephone, a web appliance, a server, a network router, switch or bridge, or any machine capable of executing the computer application 14 or another other set of instructions (sequential or otherwise) that specify actions to be taken by that machine. Further, the term "machine" shall also be taken to include any collection of machines that individually or jointly execute a set (or multiple sets) of instructions to perform any one or more of the methodologies discussed herein.

The exemplary machine may include a processing device, a main memory (e.g., read-only memory (ROM), flash memory, dynamic random access memory (DRAM) (such as synchronous DRAM (SDRAM) or Rambus DRAM (RDRAM), etc.), a static memory (e.g., flash memory, static random access memory (SRAM), etc.), and a data storage device, which communicate with each other via a bus.

Processing device represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device may also be one or more special-purpose processing devices such as an application specific integrated circuit (ASIC), a field programmable gate array (FPGA), a digital signal processor (DSP), network processor, or the like. Processing device is configured to execute listings manager logic for performing the operations and steps discussed herein.

Computer system may further include a network interface device (e.g., GUI). Computer system also may include a video display unit (e.g., a liquid crystal display (LCD) or a cathode ray tube (CRT)), an alphanumeric input device (e.g., keyboard, keypad), a cursor control device (e.g., mouse. touchpad), and a signal generation device (e.g., a speaker).

Data storage device may include a machine-readable storage medium (or more specifically a computer-readable storage medium) having one or more sets of instructions (e.g., reference generation module) embodying any one or more of the methodologies of functions described herein. The reference generation module may also reside, completely or at least partially, within main memory and/or within processing device during execution thereof by computer system; main memory and processing device also constituting machine-readable storage media. The reference generation module may further be transmitted or received over a network via network interface device.

Machine-readable storage medium may also be used to store the device queue manager logic persistently. While a non-transitory machine-readable storage medium is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instruction for execution by the machine and that causes the machine to perform any one or more of the methodologies of the present invention. The term "machine-readable storage medium" shall accordingly be taken to include, but not be limited to, solid-state memories, and optical and magnetic media.

The components and other features described herein can be implemented as discrete hardware components or integrated in the functionality of hardware components such as ASICs, FPGAs, DSPs or similar devices. In addition, these components can be implemented as firmware or functional circuitry within hardware devices. Further, these components can be implemented in any combination of hardware devices and software components.

Some portions of the detailed descriptions are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

The instructions may include, for example, computer-executable instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, and the like that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described therein.

In the aforementioned description, numerous details are set forth. It will be apparent, however, to one skilled in the art, that the disclosure may be practiced without these specific details. In some instances, well-known structures and devices are shown in block diagram form, rather than in detail, in order to avoid obscuring the disclosure.

The disclosure is related to an apparatus for performing the operations herein. This apparatus may be specially constructed for the required purposes or it may comprise a general purpose computing device selectively activated or reconfigured by a computer program stored therein. Such a computer program may be stored in a non-transitory computer readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards, flash memory devices including universal serial bus (USB) storage devices (e.g., USB key devices) or any type of media suitable for storing electronic instructions, each of which may be coupled to a computer system bus.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art.

What is claimed is:

1. A smartphone programmed classification method to reject low-quality input frames, comprising:
    collecting analyte sample image data representing frames of a video with a smartphone;
    extracting region of interest data of the analyte sample from the image data;
    tracking the region of interest data from frame to frame throughout the video with the smartphone;
    automatically identifying and rejecting video frames having problematic images thereon with the smartphone;
    automatically selecting non-rejected video frames; and
    outputting the selected video frames for analyte imaging time-averaged mean pixel intensity analysis.

2. The method of claim 1, wherein the non-rejected video frames have a higher correlation and lower standard error than the rejected video frames.

3. The method of claim 1, wherein the collected image data includes video of a well plate having an analyte sample within the well plate.

4. The method of claim 1, wherein the extracting region of interest data includes using Shi-Tomasi corner detection to obtain a set of corner points, determining an optical flow for each corner point, and updating a location of a region of interest center of each frame based on the nearest corner points.

5. The method of claim 1, wherein the problematic images include blurred images, images with excessive white-balancing, images having excessive reflection.

6. A smartphone programmed color space transform method for analyzing intensity change assays, comprising:
    collecting image data of an analyte sample with a smartphone;
    extracting region of interest data of the analyte sample from the image data, the region of interest data including red, green, and blue data;
    converting the region of interest data to processed region of interest data with the smartphone, the processed region of interest data including hue-saturation-value color space data having a saturation channel corresponding to the chromatic intensity of the region of interest data; and
    quantifying the saturation channel of the processed region of interest data to determine absorbance and concentration of the analyte sample.

7. The method of claim 6, wherein the extracting region of interest data of the analyte sample includes selecting the region of interest data from the image data and isolating the selected region of interest data in a well plate or any other colorimetric assay.

8. The method of claim 6, wherein the converting the region of interest data to processed region of interest data includes transforming the red, green, and blue coordinates to hue-saturation-value color space data.

9. The method of claim 8, wherein the converting the region of interest data to processed region of interest data includes determining the arithmetic mean of pixel intensities in the saturation channel as a mean pixel intensity, and the mean pixel intensity is used in the quantifying step to quantify the analyte sample.

10. The method of claim 6, wherein the hue-saturation-value color space data includes non-normalized hue-saturation-value color space data.

11. A smartphone programmed color space transform method for analyzing intensity change assays, comprising:
    collecting analyte sample image data representing frames of a video with a smartphone;
    extracting region of interest data from the image data with the smartphone, the region of interest data including red, green, and blue data;
    tracking the region of interest data from frame to frame throughout the video with the smartphone;
    automatically identifying and rejecting video frames having problematic images thereon with the smartphone;
    automatically selecting non-rejected video frames;
    converting the region of interest data to processed region of interest data with the smartphone, the processed region of interest data including hue-saturation-value color space data having a saturation channel corresponding to the chromatic intensity of the region of interest data; and
    quantifying the saturation channel of the processed region of interest data to determine absorbance and concentration of the analyte sample.

12. The method of claim 11, wherein the non-rejected video frames have a higher correlation and lower standard error than the rejected video frames.

13. The method of claim 11, wherein the collected image data includes video of a well plate having an analyte sample within the well plate.

14. The method of claim 11, wherein the extracting region of interest data includes using Shi-Tomasi corner detection to obtain a set of corner points, determining an optical flow for each corner point, and updating a location of a region of interest center of each frame based on the nearest corner points.

15. The method of claim 11, wherein the problematic images include blurred images, images with excessive white-balancing, images having excessive reflection.

16. The method of claim 11, wherein the extracting region of interest data of the analyte sample includes selecting the region of interest data from the image data and isolating the selected region of interest data in a well plate or any other colorimetric assay.

17. The method of claim 11, wherein the converting the region of interest data to processed region of interest data includes transforming the red, green, and blue coordinates to hue-saturation-value color space data.

18. The method of claim 17, wherein the converting the region of interest data to processed region of interest data includes determining the arithmetic mean of pixel intensities in the saturation channel as a mean pixel intensity, and the mean pixel intensity is used in the quantifying step to quantify the analyte sample.

19. The method of claim 11, wherein the hue-saturation-value color space data includes non-normalized hue-saturation-value color space data.

* * * * *